United States Patent [19]

Moniz

[11] Patent Number: 5,288,491
[45] Date of Patent: Feb. 22, 1994

[54] NONI (MORINDA CITRIFOLIA) AS A PHARMACEUTICAL PRODUCT

[76] Inventor: Herbert Moniz, R.R. 2 Box 223, Kula, Maui, Hi. 96790

[21] Appl. No.: 949,994

[22] Filed: Sep. 24, 1992

[51] Int. Cl.⁵ ............................................. A61K 35/78
[52] U.S. Cl. .................................................. 424/195.1
[58] Field of Search ..................................... 424/195.1

[56] References Cited

U.S. PATENT DOCUMENTS 4,727,030  2/1988  Ishimura et al. .................... 435/182

Primary Examiner—John W. Rollins
Attorney, Agent, or Firm—Michael I. Kroll

[57] ABSTRACT

The present invention relates to a method for processing the noni plant into powder. The method for processing the noni plant into powder, includes the steps of picking the noni fruit from the tree, placing picked noni fruit in a room, washing and cleaning the noni plant, mashing the noni fruit, placing the pulp onto liner, rotating trays for five hours, rotating trays for another five hours, rotating trays for another 14 hours, and crushing and grinding dried wafers.

1 Claim, No Drawings

NONI (*MORINDA CITRIFOLIA*) AS A PHARMACEUTICAL PRODUCT

BACKGROUND OF THE INVENTION

1. Field of the Invention

The present invention relates to the Noni plant (*Morinda Citrifolia*).

More particularly, the present invention relates to the Noni plant (*Morinda Citrifolia*) as a pharmaceutical product.

2. Description of the Prior Art

Numerous innovations for plant usage have been provided in the prior art that are adapted to be used. Even though these innovations may be suitable for the specific individual purposes to which they address, they would not be suitable for the purposes of the present invention.

For example, U.S. Pat. No. 4,666,606 to Heinicke teaches a method for eliminating grease, sewage odor and hydrogen sulfide from restaurant grease traps and municipal sewage systems using xeronine. Xeronine works by stimulating the metabolism of the resident anaerobic and aerobic bacteria.

U.S. Pat. No. 4,409,144 to Heinicke teaches that many commercial enzyme preparations which are used in pharmacology and industry and which are labeled and sold as proteases, pepidases, amylases or lysozymes actually owe their efficacy to chance contamination with the precursor system which produces Xeronine. Since the amount of the Xeronine precursor system varies between different batches of product may by the same manufacturer, the effectiveness of such products is unreliable. It is now proposed that either pure xeronine or a reliably standardized system or "kit" which releases xeronine be produced and used in place of these improperly described products.

SUMMARY OF THE INVENTION

Accordingly, it is an object of the present invention to provide a pharmaceutical plant product that avoids the disadvantages of the prior art.

The noni plant was an integral part of ancient Hawaiian folk medicine. Recently it has been regaining popularity as an herbal treatment, and is beginning to show resurgence as a cultivated plant.

Noni grows as a shrub or a tree seldom more than 10 feet tall. It has shiny, dark green leaves about eight inches long. The fruits resemble small breadfruits that turn yellow and have a strong, pungent odor when ripe.

The noni, also known as Indian mulberry, is native to Asia, Australia, and some Pacific Islands. Ancient Polynesians transported it to Hawaii to use the leaves, fruit, and bark as medicine. They also used the bark as a red dye and the root as a yellow dye.

Ripe fruits were placed in containers and left in the sun for several days to allow the juice to seep out. The extracted juice was diluted with water and taken as a drink before meals and between resting times. Noni was used in the treatment of diabetes, heart trouble, high blood pressure, kidney and bladder disorders. The plant was also used as a poultice, applied to sores and cuts, and as a treatment for boils similar to the use of magnesium sulfate. An unpleasant smelling oil was extracted from the fruit and applied to hair. In times of famine the fruit was boiled and eaten.

Fijians eat the fruit both raw and cooked. The leaves have been used to treat diarrhea, menstrual problems and fever. In the Caribbean, the leaves are steamed and applied topically for aches, pains, and tendonitis.

In keeping with these objects, and with others which will become apparent hereinafter, one feature of the present invention resides, briefly stated, in a method for processing the noni plant into powder, including the steps of, picking the noni fruit from the tree, placing picked noni fruit in a room, washing and cleaning the noni plant, mashing the noni fruit, placing the pulp onto liner, rotating trays for five hours, rotating trays for another five hours, rotating trays for another 14 hours, and crushing and grinding dried wafers.

In accordance with another feature of the present invention the picking step is initiated when the tree is half ripened.

Another feature of the present invention is that the placing step is into a dark closed room.

Yet another feature of the present invention is that the first rotating step is set at 155°.

Still another feature of the present invention is that the second rotating step is set at 145°.

Yet still another feature of the present invention is that the third rotating step is set at 135°.

The novel features which are considered characteristic for the invention are set forth in particular in the appended claims. The invention itself, however, both as to its construction and its method of operation, together with additional objects and advantages thereof, will be best understood from the following description of the specific embodiment.

DETAILED DESCRIPTION OF THE PREFERRED EMBODIMENT

It seems that within a few months the praises and claims of the fruit of the noni plant (*Morinda Citrifolia L.rubiaceae*) or commonly known as "Indian mulberry" have spread through urban Honolulu.

The Office of Hawaiian Health in the Department of Health receives at least one inquiry a month regarding how to get the fruit or plants, what it will cure, and how to prepare it.

Noni has widespread distribution in the Pacific. Researchers from the Indian subcontinent have reported widespread usage of noni among "tribal" peoples for medicinal purposes. Noni was also on display at the Samson exhibit of medicinal herbs during the Smithsonian Institute's Hawaii Day held at Magic Island. Noni was brought and introduced in the Hawaiian islands by Pacific Islanders before the arrival of European-American explorers and adventurers. In written Native accounts it was used for dyes (yielding a red and a yellow dye) in the production of Kapa (bark cloth). It is interesting to note that several medicinal manuscripts recorded by native persons, from the 1840's to 1920's, have a very limited use for noni, which may strongly suggest to be contrary to more recent publications claims for noni to be an "ancient" or traditional medicine.

Publications from the 1970's and on claim that most parts (leaves, fruit, stem, bark and root) of the noni plant are used for medicines. Leaves are reported to be used for poultices or that mashed fruit is drunk for ulcers. Noni is reported to have been used for more serious ailments and now seems to be the latest cure-all remedy, which may explain the tremendous interest in selling and raising plants.

A paper has been entitled, "The Pharmacologically Active Ingredient of Noni" by R. M. Heinicke of the University of Hawaii. The author reports that he found noni to be "the best raw material to use for the isolation of xeronine," a new alkaloid. He writes:

"Xeronine is a relatively small alkaloid .... It occurs in practically all healthy ... cells of plants, animals and microorganisms. Even though noni fruits have a negligible amount of free xeronine, they contain ... appreciable amounts of the precursor of xeronine ... Noni fruits also contain the inactive form of enzyme which releases xeronine from proxeronine. Unless this proenzyme becomes properly activated, however, noni juice will cause few pharmacological reactions. Fortunately if noni juice is taken on an empty stomach, the critical proenzyme escapes digestion in the stomach and enters the intestines. Here the chances are high that it may become activated."

Heinicke concludes that "since noni is a potential source of this alkaloid, noni juice can be a valuable herbal remedy. There are some practical problems, however, in using noni juice as a medicine or tonic ... the flavor of the juice made from ripe Hawaiian noni is terrible (and) another critical problem is (when to use) noni juice as a medicine. If the juice is drunk on a full stomach, it will have very little beneficial action. The pepsin and acid in the stomach will destroy the enzyme which liberates xeronine. For a seriously sick person taking the juice on an empty stomach rarely poses a problem ... however, for the average person ... timing is critical. It is recommended taking 100 ml. (roughly 3 to 4 fluid ounces) of noni juice a half hour before breakfast." Noni juice should not be taken with coffee, tobacco or alcohol and it would be preferred to use only the green fruit as it has more of the potentially valuable components and less of the undesirable flavor.

There are several people who swear by the curative properties of noni and there are those who will have nothing to do with it at all, particularly to drink it.

Processing Noni Into Powder

The best noni fruit is known to be grown in the Coastal areas. This is because the salt air enhances the potency of the noni fruit. Therefore the fruit used comes only from the Coastal area.

Noni fruit must be picked from the tree half ripened.

Then the half ripened fruit is placed in a closed room to be fully ripened; This method of processing noni fruit into powder is unique, because it takes away the foul smell and taste and this way it makes it more palatable for consumption.

Wash and clean the noni thoroughly removing spots and bruises.

Mash and put fruit into sieve separating seeds.

Now noni is in pulp form.

Pulp is then placed onto liner and set into dehydrating trays, the amount of pulp is spread ¼" thick for even drying (or it will burn if too thin or not dry properly if its too thick).

For the first 5 hours, the temperature is set at 155°, rotating trays in that period of time.

For the second 5 hours the temperature is reduced to 145° continuing to rotate the trays again.

For the third stage the temperature is set at 135° for fourteen hours until done. These temperatures and changes in timings are very important for even drying and is also unique in holding in and preserving its natural values.

In the final process, remove dried wafers from linear crushing wafer into small piece, placed in a grinder and ground into powdered form.

It will be understood that each of the elements described above, or two or more together, may also find a useful application in other types of constructions differing from the type described above.

While the invention has been illustrated and described as embodied in plant usage, it is not intended to be limited to the details shown, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

I claim:

1. A process for processing the noni plant into powder, that takes away the foul smell and taste and makes the fruit more palatable for human consumption; comprising the steps of:
   a) picking the noni fruit from the tree when the fruit is half ripened, placing half ripened picked noni fruit in a closed dark room until the half ripened picked fruit is fully ripened;
   b) washing and cleaning the noni plant;
   c) mashing the noni fruit;
   d) placing the pulp onto liner;
   e) rotating trays for five hours @ 155 degrees, rotating trays for another five hours @ 145 degrees, rotating trays for another 14 hours @ 135 degrees, so that these temperatures and changes in timing are very important for even drying and is also unique in holding in and preserving its natural values; and
   f) crushing and grinding dried wafers.

* * * * *